United States Patent [19]
Reif et al.

[11] 3,940,445
[45] Feb. 24, 1976

[54] PRODUCTION OF 2-METHYL-4-HALOBUT-2-EN-1-ALS
[75] Inventors: Werner Reif, Frankenthal; Roman Fischer; Horst Pommer, both of Ludwigshafen, all of Germany
[73] Assignee: Badische Anilin- & Soda-Fabrik Aktiengesellschaft, Ludwigshafen (Rhine), Germany
[22] Filed: Oct. 15, 1970
[21] Appl. No.: 81,143

[30]     Foreign Application Priority Data
    Oct. 18, 1969   Germany............................ 1952649

[52] U.S. Cl. ........................................ 260/601 H
[51] Int. Cl.² ......................................... C07C 47/14
[58] Field of Search .............................. 260/601 H

[56]             References Cited
            UNITED STATES PATENTS
2,057,964   10/1936   Muller ............................ 260/601 H
3,205,267    9/1965   Reicheneder et al. ........... 260/601 H
3,347,930   10/1967   Freyschlag et al. ................. 260/602

FOREIGN PATENTS OR APPLICATIONS
982,643   10/1965   United Kingdom............. 260/601 H OTHER PUBLICATIONS
Bull. Soc. Chim., Vol. 12, pp. 843–845, 1945, J. Jacques.
Castro et al., Jour. of Org. Chem., Vol. 30, 1965, pp. 587–592.
Degering et al., An Outline of Organic Chem., 3rd Edit., 1939, pp. 35–36.
Groggins, Unit Processes in Organic Synthesis, 4th Edit., 1952, pp. 176–178.

Primary Examiner—James O. Thomas, Jr.
Assistant Examiner—R. H. Liles
Attorney, Agent, or Firm—Johnston, Keil, Thompson & Shurtleff

[57]            ABSTRACT
A process for the production of 2-methyl-4-halobut-2-en-1-als by reacting 2-methylbut-3-en-1-al-2-ol or an acetal or acylate thereof at a temperature of from −10°C to +100°C in the presence of copper or a copper salt with the appropriate hydrogen halides.

9 Claims, No Drawings

PRODUCTION OF 2-METHYL-4-HALOBUT-2-EN-1-ALS

The present invention relates to a new process for the production of 2-methyl-4-halobut-2-en-1-als (ω-halotiglaldehydes) having the general formula:

$$O=CH-C(CH_3)=CH-CH_2-Hal \quad (I)$$

where Hal denotes chlorine or bromine.

It is known from German Pat. No. 1,188,577 that 2-methylbut-3-en-1-al-2-ol (II):

or an acetal or acylate thereof can be converted into compound (I) in the presence of tertiary amines with thionyl chloride, phosgene or thionyl bromide.

Although this method gives satisfactory yields it is not particularly economical because it necessitates fairly expensive halogenation agents and halogenation assistants and because the processing of the reaction mixture consisting of several components, although not difficult, is troublesome. Furthermore, the assistants can only be recovered at considerable expense if it is worth recovering then at all.

The object of the invention is therefore to prepare tiglaldehyde derivatives (I) — which are extremely important for the synthesis of terpenoid compounds — by a simpler method.

We have now found that compounds having the formula (I) are obtained in a remarkable reaction by treating compounds having the formula (II) with a hydrogen halide H-Hal at from −10°C to +100°C in the presence of copper or a copper salt.

The starting material (II) may be the free aldehyde or an acetal thereof with an alkanol or alkandediol such as a dialkylacetal, 1.2-alkylene acetal, or 1,3-alkylene acetal, or a dialkyl acylate thereof. The type of these functional groups is without any influence on the reaction because they are eliminated anyway during the reaction according to the invention.

Preferred alkanols are those having one to four carbon atoms, preferred alkanediols are those having two to four carbon atoms and the preferred acyl radicals are the radicals of aliphatic monocarboxylic acids having two to four carbon atoms. Particularly suitable alkyl radicals are the methyl and ethyl radicals, and the preferred acyl radical is the acetyl radical. Hydrogen chloride and hydrogen bromide are suitable as the hydrogen halides H-Hal.

The free hydrogen halides may be used but in this case the halogen ion concentration is too low for a rapid reaction. It is therefore expedient to use concentrated solutions of hydrogen halides in water, i.e. aqueous solutions of hydrogen halides which are saturated at room temperature at standard pressure, the amount used being from 0.5 to 5 times the weight of (II).

In order to increase the concentration of halogen ions still further it is even advantageous to use an alkali metal halide or alkaline earth metal halide derived from the corresponding hydrogenhalide in an amount of up to 50% by weight of the compound (II) as an additional component of the reaction mixture. The salts of sodium, potassium, magnesium and calcium, such as common salt, magnesium chloride, calcium chloride or potassium bromide, are particularly suitable as alkali metal or alkaline earth metal halides. It is also possible to pass the appropriate hydrogen halide into the concentrated aqueous hydrogen halide solution during the reaction.

The copper may be either in metallic finely divided form, for example as copper chips or copper powder, or in the form of cupric salts or cuprous salts. Copper sulfate, copper acetate, copper nitrate or a copper halide are suitable copper salts. It is preferred to use copper powder having an average particle size of less than 100 microns and cupric chloride, cupric bromide, cuprous chloride and cuprous bromide. Catalytic effectiveness has not been observed to depend on the type of anion in the copper salt; the reaction is somewhat accelerated, however, by the use of water-soluble salts when aqueous acids are used as the halogenating agent. Similarly, the amount of copper is not critical but in industrial use the preferred amounts are from 0.1 to 10% by weight based on the amount of copper and with reference to the compound (II).

The reaction may be carried out without a solvent or diluent or in the presence of the same, for example in an inert organic liquid such as an aliphatic, aromatic or chlorinated aliphatic hydrocarbon. Since it is preferred to use solutions of hydrogen halides in water, the reaction mixture is usually heterogeneous, for which reason intense stirring is advisable. It is possible to permit the reaction to proceed at least partly in the same phase, by using a water-soluble organic solvent, for example acetone or tetrahydrofuran.

The preferred temperature range for the reaction is 20° to 70°C. It is of special industrial importance to use room temperature, thus saving energy costs. The desired compounds are obtained after reaction periods of from about two to eight hours, preferably from 3 to 6 hours and after conventional working up, for example by separation, washing and drying the organic phase followed by fractional distillation at subatmospheric pressure. Yields range from 50 to 75%. It is often advisable to dilute with water the reaction mixture immediately obtained to facilitate phase separation prior to further working up.

Since the reaction is normally heterogeneous and the halogenating agent and catalyst can easily be separated from the phase consisting of compounds (I) and (II) and any solvent used, the process is particularly well suited for continuous operation.

The products of the process are important intermediates for organic syntheses of terpenoid compounds, especially vitamin A.

The following Examples illustrate the invention.

EXAMPLE 1

A mixture of 730 g of 1,1-dimethoxy-2-methylbut-3-en-2-ol, 730 g of toluene, 25 g of cuprous chloride, 250 g of sodium chloride and 1000 g of 36% hydrochloric acid is stirred for five hours at 50°C, the mixture is then diluted with 1 liter of water, and the separated organic phase is removed, washed with water until neutral, dried with sodium sulfate and subjected to fractional distillation at subatmospheric pressure. 2-Methyl-4-chlorobut-2-en-1-al is obtained in a yield of 76.0%.

EXAMPLE 2

A mixture of 146 g of 1,1-dimethoxy-2-methylbut-3-en-2-ol, 150 g of chloroform, 1 g of copper powder and 200 g of concentrated hydrochloric acid is stirred for 5 hours at 50°C and the product is worked up by a conventional method. The yield of 2-methyl-4-chlorobut-2-en-1-al is 66%.

EXAMPLE 3

417 G of 40% hydrobromic acid is added at 25° to 30°C to 146 g of 1,1-dimethoxy-2-methylbut-3-en-2-ol, 150 g of toluene, 100 g of sodium bromide and 5 g of cupric bromide and the whole is stirred for 5 hours at 30°C. The organic phase is separated and worked up by distillation in the conventional way into 2-methyl-4-bromobut-2-en-1-al which is obtained in a 52% yield.

EXAMPLE 4

100 G of 2-methylbut-3-en-1-al-2-ol is dripped at 25° to 30°C into a mixture of 100 g of benzene, 3 g of cuprous chloride and 200 g of concentrated hydrochloric acid. The mixture is stirred for another three hours at 25° to 30°C and then worked up. The yield of 2-methyl-4-chlorobut-2-en-1-al is 61%.

EXAMPLE 5

A mixture of 202 g of 1,1-diacetoxy-2-methylbut-3-en-2-ol, 250 g of toluene, 5 g of cupric chloride, 50 g of calcium chloride and 200 g of 36% hydrochloric acid is stirred for 5 hours at 50°C. 2-methyl-4-chlorobut-2-en-1-al is obtained in a yield of 68% after working up.

We claim:

1. A process for the production of a 2-methyl-4-halobut-2-en-1-al having the formula O=CH—C(CH$_3$)=CH—CH$_2$—Hal where Hal denotes chlorine or bromine by reacting at a temperature in the range of −10°C. to +100°C. in a reaction mixture consisting essentially of A. a compound selected from the group consisting of 2-methylbut-3-en-1-al-2-ol, diacetals thereof of alkanols having one to four carbon atoms, acetals thereof of alkanediols having two to four carbon atoms and acylates thereof of monocarboxylic acids having two to four carbon atoms; with B. a hydrogen halide selected from the group consisting of hydrogen chloride and hydrogen bromide in the form of a concentrated aqueous solution of said hydrogen halide, and C. in the presence of finely divided copper or a copper salt.

2. A process as claimed in claim 1 wherein said concentrated aqueous solution of (B) is added in an amount which is about 0.5 to 5 times the amount by weight of compound (A).

3. A process as claimed in claim 1 wherein the starting material is 1,1-dimethoxy-2-methylbut-3-en-2-ol.

4. A process as claimed in claim 1 wherein the starting material is 1,1-diacetoxy-2-methylbut-3-en-2-ol.

5. A process as claimed in claim 1 wherein the starting material is 2-methylbut-3-en-1-al-2-ol.

6. A process as claimed in claim 1 wherein the copper salt is cuprous chloride.

7. A process as claimed in claim 1 wherein the copper salt is cupric bromide.

8. A process as claimed in claim 1 wherein the copper or copper salt is added in an amount of from 0.1 to 10%, calculated as copper, with reference to the weight of compound (A).

9. A process as claimed in claim 1 wherein said reaction mixture additionally contains an amount up to 50% by weight based on compound (A) of an alkali metal halide or an alkaline earth metal halide, the halide ion of which corresponds to the halide of said hydrogen halide (B).

* * * * *